(12) United States Patent
Eisenhuth et al.

(10) Patent No.: US 7,954,643 B2
(45) Date of Patent: Jun. 7, 2011

(54) USE OF A DERIVATIVE OF ASPARTIC ACID AS A COLLECTOR IN FROTH FLOTATION PROCESSES

(75) Inventors: Ludwig Eisenhuth, Obernburg (DE); Elisabeth Henriksson, Kode (SE); Anders Klingberg, Hanån (SE)

(73) Assignee: Akzo Nobel N.V., Arnhem (NL)

( * ) Notice: Subject to any disclaimer, the term of this patent is extended or adjusted under 35 U.S.C. 154(b) by 1435 days.

(21) Appl. No.: 10/578,106

(22) PCT Filed: Nov. 5, 2004

(86) PCT No.: PCT/EP2004/012744
§ 371 (c)(1),
(2), (4) Date: May 3, 2006

(87) PCT Pub. No.: WO2005/046878
PCT Pub. Date: May 26, 2005

(65) Prior Publication Data
US 2007/0071665 A1   Mar. 29, 2007

(30) Foreign Application Priority Data
Nov. 13, 2003   (SE) ........................................ 0302986

(51) Int. Cl.
*B03D 1/01* (2006.01)
*B03D 1/02* (2006.01)
(52) U.S. Cl. ........................................ 209/166
(58) Field of Classification Search ................. 209/166, 209/167
See application file for complete search history.

(56) References Cited

U.S. PATENT DOCUMENTS

| | | | | |
|---|---|---|---|---|
| 2,200,220 A | | 5/1940 | Reppe et al. ................. 260/534 |
| 3,830,366 A | * | 8/1974 | Day et al. ...................... 209/166 |
| 4,043,902 A | | 8/1977 | Hartjens et al. .............. 209/166 |
| 4,199,064 A | * | 4/1980 | Holme ............................. 209/5 |
| 4,358,368 A | | 11/1982 | Hellsten et al. ............... 209/167 |
| 4,790,932 A | | 12/1988 | Kottwitz et al. .............. 209/166 |
| 6,054,260 A | | 4/2000 | Adin et al. .................... 430/583 |
| 6,077,962 A | | 6/2000 | Prakash et al. ................ 549/253 |

FOREIGN PATENT DOCUMENTS

| | | |
|---|---|---|
| DE | 3511678 A1 | 10/1985 |
| JP | 05140059 | 6/1993 |
| JP | 2000136172 | 5/2000 |

OTHER PUBLICATIONS

English translation of Japanese Patent Application No. 2001-136172, published May 16, 2000.
International Search Report for International Application No. PCT/EP2004/012744, May 3, 2005.
Derwent Abstract of JP 2000136172.
CAPLUS accession No. 1993:581234, document No. 119:181234.
Derwent Abstract of DE 3511678 A1.
CAPLUS accession No. 1991:822448, document No. 114:82448.
CAPLUS accession No. 1995:721486, document No. 123:122759.
CAPLUS accession No. 1997:476570, document No. 127:220944.

* cited by examiner

Primary Examiner — Thomas M Lithgow
(74) Attorney, Agent, or Firm — Ralph J. Mancini

(57) ABSTRACT

A derivative of aspartic acid is used as a collector for a phosphate containing mineral, such as apatite, in a froth flotation process. According to the invention the collector has a high selectivity for phosphate containing minerals even in the presence of carbonate minerals, such as calcite. The derivative has the formula (I) where $R^I$ is a hydrophobic group containing a hydrocarbon group of 6-24 carbon atoms; $R^{II}$ is an alkyl group with 1-7 carbon atoms or a group of the formula $(B)_yH$, in which B is an alkyleneoxy group with 2-4 carbon atoms and y is a number from 1 to 10; and M is a group selected from the group consisting of a cation or hydrogen. Methods for producing the derivative are also described.

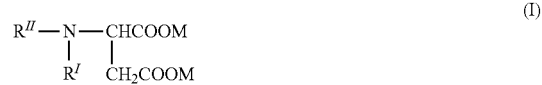

(I)

9 Claims, No Drawings

USE OF A DERIVATIVE OF ASPARTIC ACID AS A COLLECTOR IN FROTH FLOTATION PROCESSES

This case was filed under the Patent Cooperation Treaty on Nov. 5, 2004, and claims priority of Swedish patent application No. 0302986-5 filed on Nov. 13, 2003.

The present invention relates to the use of a derivative of aspartic acid as a collector for a phosphate containing mineral, such as apatite, in a froth flotation process. According to the invention the collector has a high selectivity for phosphate containing minerals even in the presence of carbonate minerals, such as calcite. A method for the manufacture of the derivatives as well as specific aspartic derivates are also disclosed.

Phosphate rocks contain calcium phosphate minerals largely in the form of apatite usually together with other minerals for example silicate minerals and carbonate minerals, such as calcite. Apatite is a generic name for a group of calcium phosphate minerals also containing other elements or radicals such as fluorapatite, chlorapatite, carbonate apatite and hydroxyl apatite.

It is well-known to separate the valuable phosphate minerals from the barren minerals by using a froth flotation process where the phosphate minerals are enriched in the float. In these flotation processes fatty acids and naphtenic acids and their soaps have frequently been used as a collector. However, this type of collectors works well only when silicate minerals are the barren mineral. When carbonate minerals, such as calcite, are present in the ore, a low selectivity for the phosphate minerals is obtained. The selectivity can to a certain degree be improved by the concurrent use of depressants, such as polysaccharides of different types.

Anionic surfactants such as alkylbenzene sulphonates, alkyl phosphates and alkyl sulphosuccinamates have also been proposed as flotation agents for phosphate containing ores, but their selectivity for and yield of calcium phosphate in froth flotation processes are still too low.

In U.S. Pat. No. 4,358,368 it is disclosed that the selectivity for calcium phosphate minerals can be essentially improved by using amphoteric surfactants of the sarcosinate type. The sarcosinate is advantageously used in combination with a nonionic, water-insoluble polar co-collector. The drawback of sarcosinate as a collector is the fact that it has limited ability to fasten to the apatite surfaces which limits the yield of apatite in the concentrate.

Further, the U.S. Pat. No. 4,043,902 discloses a process for froth flotation of non-sulfide ores such as sulfates, carbonates, fluorides, tungstates, phosphates and oxides, e.g. celestite, barite, sheelite, fluorite, calcite, magnesite, gypsum, anhydrite, cassiterite, apatite and the like, using salts of tri- and tetra-carboxyl containing fatty alkyl substituted aspartic acids, aspartic mono-esters, and aspartic di-esters, as collectors in conjunction with appropriate gangue depressants where required.

The U.S. Pat. No. 4,790,932 describes a process for the froth flotation of non-sulfidic mineral containing ores, in which process an anionic and/or nonionic collector surfactant is used as a collector in conjunction with at least one N-alkyl or N-alkenyl aspartic acid as a co-collector.

Several publications also disclose aspartic derivatives for other uses than as collectors in, froth flotation processes. For instance, CAPLUS accession 1995:721486, document No. 123:122759 discloses compositions containing amide derivates of aspartic acids, which compositions are said to be useful for the body and face skins. The publication CAPLUS accession No. 1993:581234, document No. 119:181234 describes a process for the preparation of N-substituted derivatives of aspartic acid, the substituents being C8-C22 alkyl or alkenyl or $(CH_2)_3OC8$-C22 alkyl or alkenyl; and C1-C22 alkyl or alkenyl, which may be substituted with —OH, —COOH or —$SO_3H$. The U.S. Pat. No. 6,077,962 discloses derivatives of aspartic acid containing one or two 3,3-dimethylbutyl groups bond to the nitrogen atom.

Other examples of derivatives of aspartic acid can be found in CAPLUS accession No. 1991:82448, document No. 114:82448, CAPLUS accession No.1997:476570, documents No. 127:220944, U.S. Pat. No. 6,054,260 and DE patent application No. 35 11 678 A1.

According to the present invention it has now been found that a certain derivative of aspartic acid has excellent properties as a collector for a calcium phosphate-containing mineral in an alkaline froth flotation process of an ore also containing calcium carbonate. The derivative of the invention has the formula

(I)

where $R^I$ is a hydrophobic group containing a, preferably monovalent, hydrocarbon group of 6-24 carbon atoms; $R^{II}$ is an alkyl group with 1-7 carbon atoms, preferably 1-3 carbon atoms, or a group of the formula $(B)_yH$, in which B is an alkyleneoxy group with 2-4 carbon atoms and y is a number from 1 to 10, preferably from 1 to 3; and M is a group selected from the group consisting of a cation or hydrogen. The nitrogenation in formula I is suitably a tertiary nitrogen atom. According to the invention $R^I$ is preferably a glycidylether group of the formula $CH_2CH(OH)CH_2O(A_1)_{x1}R_1$, in which $R_1$ is a hydrocarbon group with 8-24 carbon atoms, $A_1$ is an alkyleneoxy group with 2-4 carbon atoms and x1 is a number from 0 to 10, preferably from 0 to 5; a hydroxyl group of the formula $CH_2CH(OH)R_2$, in which $R_2$ is a hydrocarbon group with 6-22 carbon atoms; a propylene ether group of the formula $C_3H_6O(A_3)_{x3}R_3$, in which $R_3$ is a hydrocarbon group with 8-24 carbon atoms, A3 is an alkyleneoxy group with 2-4 carbon atoms and x3 is a number from 0-10, preferably from 0 to 5, or a number from 1-5; or a group of the formula $R_4$, where $R_4$ is a hydrocarbon group containing 8-24 carbon atoms. Suitably the group $(A_1)_{x1}R_1$ is $(C_2H_4O)_{1-3}R_1$, where $R_1$ is a hydrocarbon group of 10-20 carbon atoms, such as an aliphatic group or an alkylphenyl group, while x3 is zero or a number from 1-3. Most preferably $R^{II}$ is methyl, hydroxyethyl or hydroxypropyl. The cation M is normally a monovalent cation, such as sodium, potassium or an ammonium cation. The amount of the derivative can vary within wide limits but is normally between 10 and 1500, preferably between 50 and 800, grams per ton of the ore.

The froth flotation process of the invention results in a high concentration and a high yield of calcium phosphates in the float. The derivatives of the invention are suitably used in combination with a nonionic, water-insoluble polar compound as a co-collector, whereby the selectivity and the yield is further improved. The polar co-collector has a good affinity for the particles coated with the derivative and can thereby improve or further enhance the properties of the derivative. The co-collector can be used in amounts between 0 and 1000, preferably between 5 and 350, grams per ton of the ore.

The derivative of the invention can be manufactured by reaction steps well-known to a person skilled in the art. For example, under alkaline conditions, maleic acid or a salt thereof can be reacted with a) a primary amine of the formula $R^{II}NH_2$, where $R^{II}$ has the meaning mentioned in formula I, followed by reacting the intermediate obtained with a glycidylether of the formula

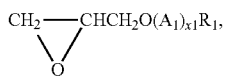

where $R_1$, x1 and $A_1$ have the meanings mentioned above, an epoxide of the formula

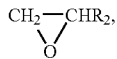

where $R_2$ has the meaning mentioned above, or a halide compound of the formula $HalR_4$, where Hal is a halide and $R_4$ has the meaning above; or b) with a primary amine of the formula $R^I NH_2$, where $R^I$ has the meaning mentioned in formula I, followed by reacting the intermediate obtained with a halide compound of the formula $HalR^{II}$, where Hal is a halide and $R^{II}$ has the meaning mentioned above.

A more specific method of producing the derivative according to the invention is to react for example the disodium salt of maleic acid with methylamine to obtain the N-methylaspartic acid disodium salt. This reaction product can then be further reacted with a compound

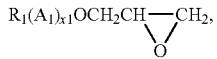

where $R_1$, $A_1$ and x1 have the meanings mentioned above, to obtain an aspartate of the formula

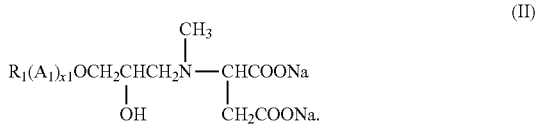

(II)

Another method is to react the intermediate product, N-methylaspartate disodium salt, with a compound of the formula

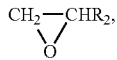

where $R_2$ has the meaning mentioned above, to an aspartate of the formula

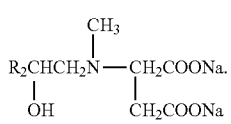

(III)

Still another method is to first react the monosodium salt of maleic acid with a compound of the formula $R_3(A_3)_{x3}$ $OC_3H_6NH_2$, where $R_3$, $A_3$ and x3 have the meanings mentioned above, to obtain an aspartate intermediate of the formula

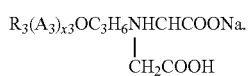

The intermediate can then be reacted with $ClCH_2CH_2OH$ or $CH_3Cl$ and NaOH to form a derivative of the formulae

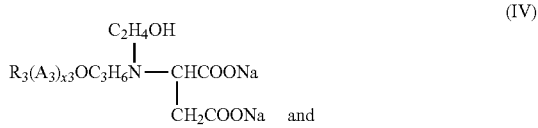

(IV)

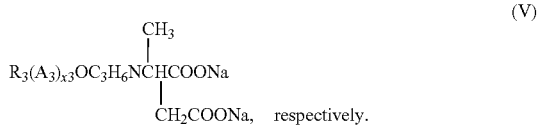

(V)

respectively.

The present invention also comprises specific derivatives of aspartic acid of formula I, where $R^I$ is a hydrophobic group containing a monovalent hydrocarbon group of 6-24 carbon atoms; $R^{II}$ is an alkyl group with 1-7 carbon atoms or a group of the formula $(B)_yH$, in which B is an alkyleneoxy group with 2-4 carbon atoms and y is a number from 1 to 10; and M is a group selected from the group consisting of a cation or hydrogen, with the proviso that when $R^{II}$ is an alkyl group with 1-7 carbon atoms then $R^I$ is not a group RCO, where R is a C7-C21 alkyl or alkenyl, a group R, where R is a C8-C22 alkyl or alkylene group, or a group $(CH_2)_3OR$, where R is a C8-C22 alkyl or alkylene group.

Suitable compounds of formula I are those where $R^I$ is a glycidylether group of the formula $CH_2CH(OH)CH_2O(A_1)_{x1}R_1$, in which $R_1$ is a hydrocarbon group with 8-24 carbon atoms, $A_1$ is an alkyleneoxy group with 2-4 carbon atoms and x1 is a number from 0 to 10; a hydroxyl group of the formula $CH_2CH(OH)R_2$, in which $R_2$ is a hydrocarbon group with 6-22 carbon atoms; a propylene ether group of the formula $C_3H_6O(A_3)_{x3}R_3$, in which $R_3$ is a hydrocarbon group with 8-24 carbon atoms, $A_3$ is an alkyleneoxy group with 2-4 carbon atoms and x3 is a number from 0-10, or a group of the formula $R_4$.

More specific example of derivates are those selected from the group consisting of

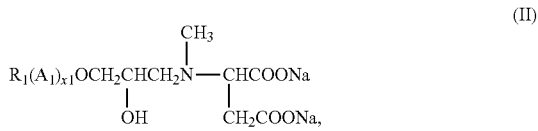

(II)

where $R_1$, $A_1$ x1 have the same meanings as above,

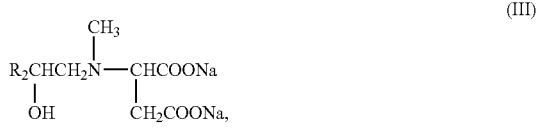

(III)

where $R_2$ has the same meaning as in claim 2,

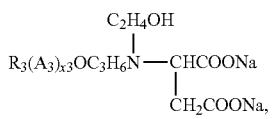 (IV)

where $R_3$, $A_3$ and x3 have the same meanings as above, and

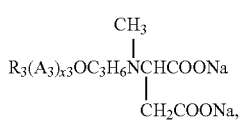 (V)

where $R_3$, $A_3$ and x3 have the same meanings as above, or a mixture of two or more of the derivatives of formula II, III, IV or V.

The polar co-collector to be used in combination with the aspartic acid derivative of the invention is suitably an alkylene oxide adduct of the formula $$R^{III}(A)_p OH \quad (VI),$$

in which $R^{III}$ is a hydrocarbon group, preferably an aliphatic group or an alkylphenyl group, with 8-22 carbon atoms, A is an oxyalkylene group having 2-4 carbon atoms and p is a number from 1-6. The oxyalkylene groups are suitably oxyethylene groups or a mixture of oxyethylene and oxypropylene groups. By placing the oxypropylene groups and especially the oxybutylene groups in the end position of the adduct, a lower foaming is achieved.

Another suitable co-collector is an ester of the formula

 (VII)

in which $R^{IV}$ is an aliphatic group having 7-21 carbon atoms, A is an alkyleneoxy group having 2-4 carbon atoms, q is a number from 0-6, and Y is an alkyl group having 1-4 carbon atoms or hydrogen, provided that Y cannot be hydrogen when q is zero.

In addition to their advantageous froth flotation effect, the co-collectors also have a favourable effect on foaming by making the foam less stable when used in combination with the derivative of the invention.

In the process according to the invention, it is also possible to add pH-adjusting substances, such as sodium carbonate and sodium hydroxide, foaming agents, foam regulators, depressants, such as waterglass, different types of starch and CMC, and activating substances. In the present froth flotation process the pH-value of the pulp is suitably within the range of 8-11.

The present invention is further illustrated by the following working examples.

EXAMPLE 1

A magmatic ore, containing about 12% by weight of fluorapatite and about 73% by weight of calcite and a rest containing silicates and magnetite, was ground to a particle size of $\leq 630$ μm. The ground ore in an amount of 390 grams, 0.8 liter of water and 78 mg of hydrolysed corn starch dissolved in an amount of 1% by weight in water, were added to a flotation cell of 1.5 liter, whereupon the pH value was adjusted to 10.5 by addition of NaOH and the ground ore was conditioned for 5 minutes at 23° C. After the conditioning, 78 mg of a reagent according to the table below was added as a 1% by weight solution in water and the total amount in the flotation cell was adjusted by addition of water to 1.4 liter. The content of the flotation cell was then conditioned for 2 minutes, followed by a rougher flotation step and one or more cleaning steps of the rougher concentrates.

The rougher concentrate and the concentrates from the cleaning steps were analysed with regard to their contents of phosphate ($P_2O_5$) and calcite. The results obtained are shown in Table II below.

TABLE I

| Code | | Reagents Composition |
|---|---|---|
| A | a) | 39% by weight of sarcosinate of the formula nonphenyl-$(C_2H_4O)_{1.1}CH_2CHCH_2N^+CH_2COO^-$ with OH and $CH_3$ and $CH_3$ substituents according to the U.S. Pat. No. 4,358,368 |
| | b) | 27% by weight of the reaction product between 1 mole of nonylphenol and 2 moles of ethylene oxide |
| | c) | 34% by weight of a solvent consisting of water and propylene glycol |
| B | a) | 39% by weight of nonylphenyl-$(C_2H_4O)_{1.1}CH_2CHCH_2NHCHCOONa$ with OH and $CH_2COONa$ substituents |
| | b) | As in reagent A, b) |
| | c) | As in reagent A, c) |
| 1 | a) | 39% by weight of nonylphenyl-$(C_2H_4O)_{1.1}CH_2CHCH_2N$—CHCOONa with $CH_3$, OH and $CH_2COONa$ substituents |
| | b) | As in reagent A, b) |
| | c) | As in reagent A, c) |
| 2 | a) | 39% by weight of  |
| | b) | As in reagent A above |
| | c) | As in reagent A above |

The reagent A represents the prior art and B is a comparison, while the aspartate-containing reagents 1 and 2 are in accordance with the invention.

TABLE II

Flotation results of reagents A, 1 and 2

| Reagent | Flotation step | Concentrate Content, % P$_2$O$_5$ | Yield, % apatite | Content, % calcite |
|---|---|---|---|---|
| A | Rougher | 18.3 | 99.0 | 43.2 |
|   | Cleaning 1 | 38.8 | 68.0 | 2.3 |
| B | Rougher | 19.9 | 93.6 | — |
|   | Cleaning 1 | 29.5 | 86.2 | — |
|   | Cleaning 2 | 36.7 | 77.9 | — |
|   | Cleaning 3 | 41.7 | 64.2 | — |
| 1 | Rougher | 17.3 | 98.5 | 43.2 |
|   | Cleaning 1 | 31.9 | 96.5 | 9.1 |
|   | Cleaning 2 | 40.2 | 92.3 | 2.0 |
|   | Cleaning 3 | 42.5 | 87.3 | 0.5 |
| 2 | Rougher | 23.2 | 94.3 | 41.4 |
|   | Cleaning 1 | 34.0 | 90.8 | 15.9 |
|   | Cleaning 2 | 38.7 | 85.4 | 4.5 |
|   | Cleaning 3 | 40.2 | 78.3 | 2.0 |

The results show that the aspartate-containing reagents are superior to the reagent A in accordance with the prior art and the comparison B. The content and yield of apatite are improved, while the content of calcite is low.

EXAMPLE 2

500 g of a magnetic ore having a particle size of ≦5 μm and containing 9% by weight of fluorapatite, 17% by weight of calcite and a rest mainly consisting of silicates was ground in a rod mill together with 0.4 liter of water, 180 mg of NaOH and 50 mg of waterglass with a ratio between SiO$_2$ and Na$_2$O of 3.3:1 to a particle size, where 80% by weight of the ground ore had a particle size ≦250 μm. The ground ore, 125 mg of the reagent in Table 3, and water were added to a flotation cell of 1.5 liter, the water being added in such an amount that the total volume of the ore pulp became 1.4 liter. After adjusting the pH value to 11 by the addition of NaOH, the pulp was conditioned at 21° C. for 5 minutes. To the conditioned pulp, 25 mg of an iso-butyric acid ester of secondary butanol was added as a foamer, and a rougher flotation step was performed followed by three cleaning steps. The concentrates from the rougher flotation and from the cleaning steps were analysed with regards to the yield of apatite and the results obtained are shown in the Table IV below.

TABLE III

| Code | Reagent Composition |
|---|---|
| 3 | a) 36% by weight of an aspartate of the formula |

R—CH$_2$CHCH$_2$N—CH—CH$_2$COONa
         |           |
         OH          CH$_2$COONa
with CH$_3$ on the CH carbon where R is an aliphatic group containing 13-15 carbon atoms
b) 21% by weight of the reaction product between 1 mole of nonylphenol and 2 moles of ethylene oxide
c) 43% by weight of a solvent consisting of water and propylene glycol

TABLE IV

Flotation results of reagent 3

| Reagent | Flotation step | Concentrate Content, % P$_2$O$_5$ | Yield, % apatite |
|---|---|---|---|
| 3 | Rougher | 18.5 | 97.1 |
|   | Cleaning 1 | 23.7 | 94.8 |
|   | Cleaning 2 | 32.1 | 90.6 |
|   | Cleaning 3 | 37.5 | 74.5 |

The results show that the reagent according to the invention makes it possible to increase the content of apatite and obtain a high yield although the content of apatite in the ore is low.

The invention claimed is:

1. A froth flotation process for the enrichment of a calcium phosphate-containing mineral from an ore also containing calcium carbonate, wherein the process is performed in the presence of a collector, wherein said collector is a derivative of aspartic acid of the formula

(I)

where $R^I$ is a hydrophobic group containing a hydrocarbon group of 6-24 carbon atoms; $R^{II}$ is an alkyl group with 1-7 carbon atoms or a group of the formula $(B)_yH$, in which B is an alkyleneoxy group with 2-4 carbon atoms and y is a number from 1 to 10; and M is a group selected from the group consisting of a cation or hydrogen.

2. The froth flotation process of claim 1 wherein $R^I$ is a glycidyl ether group of the formula $CH_2CH(OH)CH_2O(A_1)_{x1}R_1$, in which $R_1$ is a hydrocarbon group with 8-24 carbon atoms, $A_1$ is an alkyleneoxy group with 2-4 carbon atoms and x1 is a number from 0 to 10; a hydroxyl group of the formula $CH_2CH(OH)R_2$, in which $R_2$ is a hydrocarbon group with 6-22 carbon atoms; a propylene ether group of the formula $C_3H_6O(A_3)_{x3}R_3$, in which $R_3$ is a hydrocarbon group with 8-24 carbon atoms, $A_3$ is an alkyleneoxy group with 2-4 carbon atoms and x3 is a number from 0-10; or a group of the formula $R_4$, where $R_4$ is a hydrocarbon group containing 8-24 carbon atoms.

3. The froth flotation process of claim 2, wherein the derivative is selected from the group consisting of

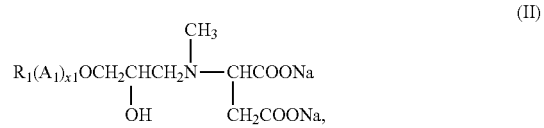

(II)

where $R_1$, $A_1$, x1 have the same meanings as in claim 2,

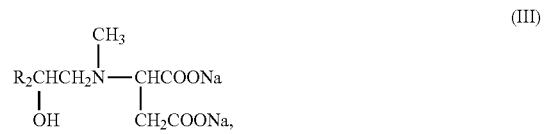

(III)

where $R_2$ has the same meaning as in claim 2,

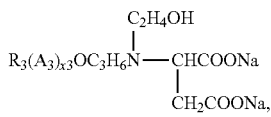
(IV)

where $R_3$, $A_3$ and x3 have the same meanings as in claim 2, and

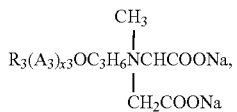
(V)

where $R_3$, $A_3$ and x3 have the same meanings as in claim 2, and mixtures of two or more of the derivatives of formula II, III, IV or V.

4. The froth flotation process of claim 2 wherein $A_1$ and $A_3$ are both ethyleneoxy and $x_1$ and $x_3$ are each independently selected from a number of from 1-4.

5. The froth flotation process of claim 1 wherein $R^{II}$ is methyl, hydroxyethyl or hydroxypropyl.

6. The froth flotation process of claim 1 wherein the derivative is present in an amount of 10-1500 grams per ton of the ore.

7. The froth flotation process of claim 1 wherein the process is performed in the presence of a polar co-collector of the formula

(VI)

in which $R^{III}$ is a hydrocarbon group with 8-22 carbon atoms, A is an oxyalkylene group having 2-4 carbon atoms and p is a number from 1-6, or of the formula

(VII)

in which $R^{IV}$ is an aliphatic group having 7-21 carbon atoms, A is an alkyleneoxy group having 2-4 carbon atoms, q is a number from 0-6, and Y is an alkyl group having 1-4 carbon atoms or hydrogen, provided that Y cannot be hydrogen when q is zero.

8. The froth flotation process of claim 3 wherein $A_1$ and $A_3$ is ethyleneoxy and $x_1$ and $x_3$ are each independently selected from a number of from 1-4.

9. The froth flotation process of claim 2 wherein $R^{II}$ is methyl, hydroxyethyl or hydroxypropyl.

\* \* \* \* \*